United States Patent [19]
Yoon

[11] Patent Number: 6,099,550
[45] Date of Patent: Aug. 8, 2000

[54] SURGICAL INSTRUMENT HAVING JAWS AND AN OPERATING CHANNEL AND METHOD FOR USE THEREOF

[76] Inventor: InBae Yoon, 2101 Highland Ridge Dr., Phoenix, Md. 21131

[21] Appl. No.: 09/063,300

[22] Filed: Apr. 21, 1998

Related U.S. Application Data

[63] Continuation-in-part of application No. 08/847,187, May 1, 1997, Pat. No. 5,984,938, which is a continuation-in-part of application No. 08/376,186, Jan. 20, 1995, Pat. No. 5,665,100, which is a continuation-in-part of application No. 08/281,814, Jul. 28, 1994, abandoned, which is a continuation of application No. 08/073,193, Jun. 8, 1993, Pat. No. 5,334,209, which is a continuation of application No. 07/720,381, Jun. 25, 1991, Pat. No. 5,217,473, which is a division of application No. 07/446,555, Dec. 5, 1989, Pat. No. 5,026,379.

[51] Int. Cl.$^7$ ..................................................... A61B 17/28
[52] U.S. Cl. ............................................ 606/205; 606/207
[58] Field of Search ................................... 606/205, 207, 606/151, 170, 142, 144, 139, 147, 148, 167

[56] References Cited

U.S. PATENT DOCUMENTS 2,002,594  5/1935  Wappler et al. ........................... 174/89
3,989,049  11/1976  Yoon ........................................ 128/326

*Primary Examiner*—Michael Buiz
*Assistant Examiner*—Julian W. Woo
*Attorney, Agent, or Firm*—Blank, Rome, Comisky & McCauley

[57] ABSTRACT

A surgical instrument includes a forceps unit for being positioned within an anatomical cavity. The forceps unit includes a housing, an outer tubular member, an intermediate tubular member, and a handle mechanism coupled with at least one of the intermediate and outer tubular members for creating relative movement between the intermediate and outer tubular members. The outer tubular member has a proximal end mounted by the housing and terminates distally at a distal end. The intermediate member has a tubular body disposed telescopically within the outer tubular member, a proximal end mounted by the housing and a pair of opposed jaws disposed on a distal end of the tubular body resiliently biased apart such that relative movement of the outer tubular member distal end over the jaws causes the jaws to close. A channel or passage is defined through the instrument to permit an inner member having an end effector to be inserted therethrough.

20 Claims, 10 Drawing Sheets

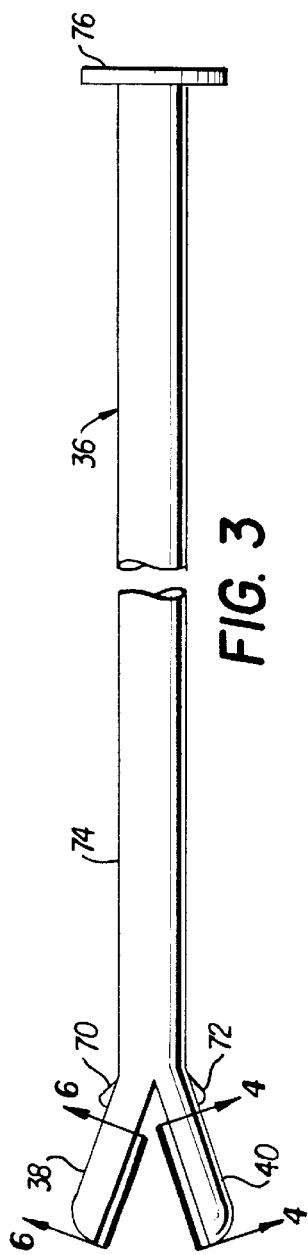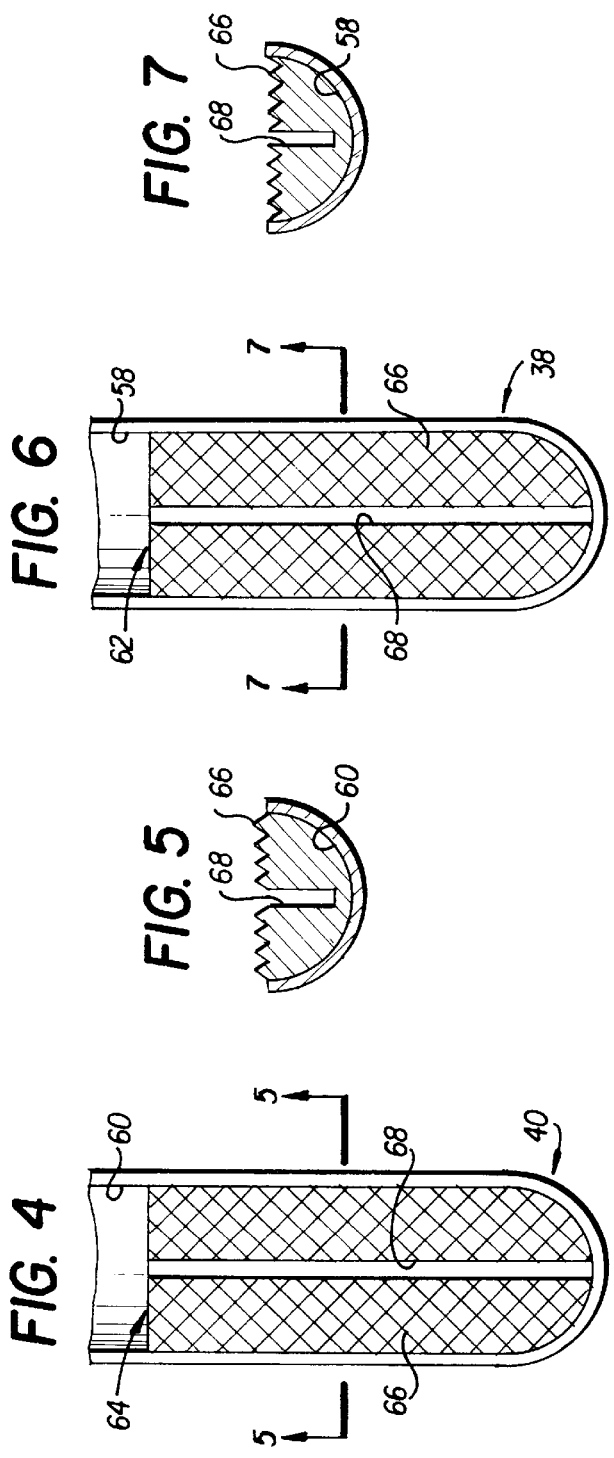

SURGICAL INSTRUMENT HAVING JAWS AND AN OPERATING CHANNEL AND METHOD FOR USE THEREOF

CROSS-REFERENCE TO RELATED APPLICATIONS

This application is a continuation-in-part of applicant's patent application Ser. No. 08/847,187, filed in May 1, 1997, now U.S. Pat. No. 5,984,938 which is a continuation-in-part of applicant's patent application Ser. No. 08/376,186, filed on Jan. 20, 1995, now U.S. Pat. No. 5,665,100 which is a continuation-in-part of applicant's patent application Ser. No. 08/281,814, filed Jul. 28, 1994 now abandoned, which is a continuation of patent application Ser. No. 08/073,193, filed Jun. 8, 1993, now U.S. Pat. No. 5,334,209, which is a continuation of patent application Ser. No. 07/720,381, filed Jun. 25, 1991, now U.S. Pat. No. 5,217,473, which is a divisional of patent application Ser. No. 07/446,555, filed Dec. 5, 1989, now U.S. Pat. No. 5,026,379, the disclosures of which are incorporated herein by reference.

BACKGROUND OF THE INVENTION

1. Field of the Invention

The present invention relates generally to surgical procedures and instruments and, more particularly, to a multi-functional instrument having jaws and a channel defined through the instrument and a method for using the instrument.

2. Discussion of the Related Art

Endoscopic or minimally invasive medical procedures, such as laparoscopic, culdescopic, and minilap procedures, have become widely accepted for surgery and diagnosis due to the associated advantages relating to reduced trauma and hospitalization time. The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, ligating appliers, forceps, cauteries and the like into the anatomical cavity.

Endoscopic, i.e. minimally invasive, procedures commonly involve performing a number of individual acts or functions within the anatomical cavity including grasping, cutting, coagulating, irrigating, aspirating, puncturing, injecting, dissecting, cauterizing, ligating, suturing, illuminating, visualizing and/or collecting specimens for biopsy. However, typical endoscopic instruments are capable of performing at most two of the above functions, requiring several incisions for placement of multiple portal sleeves to accommodate a suitable number of endoscopic instruments for performing the required functions or necessitating frequent withdrawal and replacement of individual endoscopic instruments through a single incision. While it is generally desirable to minimize the number of incisions created for performing a particular endoscopic procedure, substitution of instruments through a single incision can be time consuming, depending on the efficiency of the medical facility and staff, increasing the period of anesthetization for the patient. Additionally, internal bleeding can develop during the substitution of instruments thereby obscuring the field of view and requiring time consuming cleanup procedures to be performed. Also, it is desirable to manipulate tissue with various jaw configurations prior to and during other endoscopic procedures.

A disadvantage of endoscopic instruments having articulated jaws, in particular, is that the jaws are typically mounted on pivots at the distal end of relatively long shafts requiring complicated and space-consuming linkages for converting the user's proximal movements into motion of the jaws and increasing the risk of fluid leaking through poorly sealed pivotal mounts.

SUMMARY OF THE INVENTION

Accordingly, it is a primary object of the present invention to overcome the above mentioned disadvantages of the prior art with an instrument capable of performing multiple functions including manipulation of tissue with jaws.

Another object of the present invention is to minimize the number of punctures or incisions required for performing an endoscopic procedure by performing multiple functions through a single incision with an endoscopic instrument having a forceps unit with jaws for performing grasping and other functions and a channel for receiving movable or fixed members in the jaws or adjacent the jaws for performing at least one of the functions of, cutting, dissecting, aspirating, irrigating, penetrating, injecting, creating suction, collecting biopsy samples, hooking, manipulating and cauterizing through the forceps unit.

It is another object of the present invention to lock jaws of an endoscopic instrument together to ensure smooth entry of the endoscopic instrument through a portal sleeve and to prevent inadvertent snagging of anatomical tissue.

Some of the advantages of the present invention over the prior art are that the endoscopic instrument can perform multiple functions through a single incision thereby minimizing the number of incisions required to perform an endoscopic procedure, that use of an endoscopic instrument for picking-up and holding objects is simplified, that objects can be held without the need for exerting continuous hand or finger pressure, that single-handed operation of a forceps unit and other implements is facilitated, that conventional handle structures can be used to provide users with a familiar feel and to decrease adaptation time, that the instrument can be fabricated at low cost using simple mechanisms without complicated linkages, and that the instrument can be sterilized for reuse or disposable for single patient use as desired.

The present invention is generally characterized in an instrument including a forceps unit for being positioned within an anatomical cavity and an operating channel defined in the instrument for permitting a moveable member to be advanced through the instrument or for providing communication with the anatomical cavity. The forceps unit includes a housing, an outer member, an intermediate member, and a handle mechanism coupled with at least one of the intermediate and outer members for creating relative movement therebetween. The outer member has a proximal end mounted in the housing and terminates distally at a distal end. The intermediate member has a tubular body disposed telescopically within the outer member, a proximal end mounted in the housing and a distal end defining a pair of opposed jaws resiliently biased apart such that relative movement of the outer member distal end over the jaws causes the jaws to close. An operating channel can be defined through the intermediate member or through other portions of the instrument to allow at least one of the functions of cutting, grasping, hooking, manipulating, dissecting, collecting tissue for biopsy, penetrating, injecting, creating suction, aspirating, irrigating and cauterizing to be conducted by an inner member or instrument, inserted through the central channel. A handle provides proximal controls for the forceps unit and can be adjusted to assume various orientations with respect to the longitudinal axis of the instrument.

A further aspect of the present invention is generally characterized in a method of performing an endoscopic procedure including the steps of introducing a tubular member with jaws through an opening in an anatomical cavity wall, grasping anatomical tissue with the jaws, and performing a medical procedure involving, for example, the functions of cutting, grasping, dissecting, cauterizing, penetrating, injecting, hooking, manipulating, collecting a biopsy, irrigating and aspirating through a channel defined in the tubular member or through another portion of the instrument.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 3 illustrates the intermediate member;

FIG. 4 illustrates one of the jaws;

FIG. 5 illustrates the jaw of FIG. 4 in cross-section taken along line 5—5;

FIG. 6 illustrates the other jaw;

FIG. 7 illustrates the jaw of FIG. 6 in cross-section taken along line 6—6;

DESCRIPTION OF THE PREFERRED EMBODIMENTS

The endoscopic instrument of the present invention can be utilized in any type of anatomical cavity; and, accordingly, while the instrument is described hereinafter for use with a portal sleeve in endoscopic procedures, such as laparoscopy, the instrument can be used with catheters or, incisions or other means of accessing small cavities, such as veins and arteries, as well as large cavities, such as the abdomen. Also, the instrument can be used in open surgery.

Figure 1:
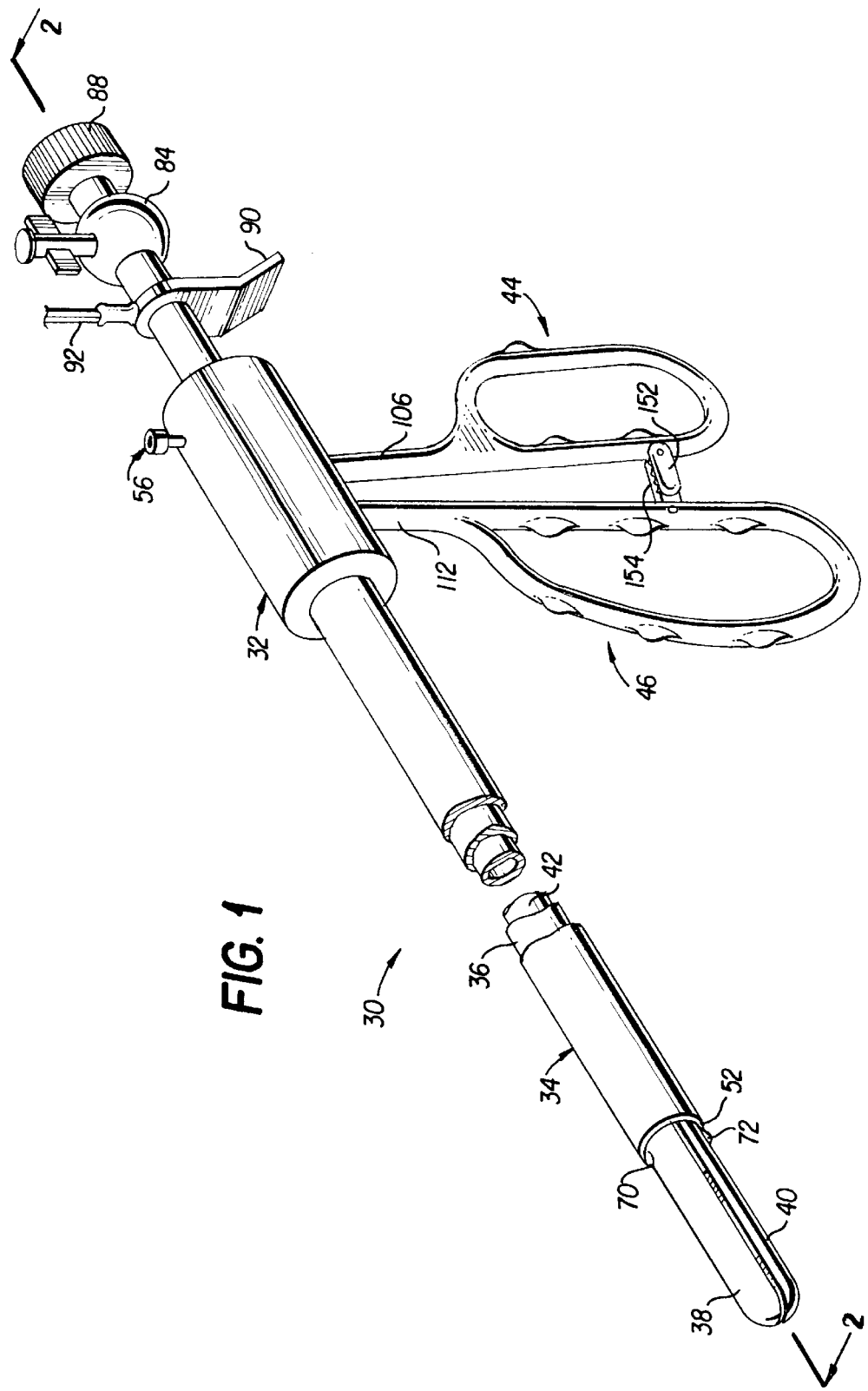
FIG. 1 is a perspective view, broken longitudinally, of an endoscopic instrument according to the present invention.

Endoscopic instrument 30 according to a first preferred embodiment of the present invention, as shown in FIG. 1, includes housing 32, tubular outer member 34 extending distally from the housing 32, tubular intermediate member 36 telescopically fitted within outer tubular member 34 and having opposed jaws 38 and 40 on a distal end thereof, and a pair of handles 44 and 46 extending from the housing at an angle relative to the longitudinal axis of the instrument. An operating channel, or lumen, is defined through intermediate member 36 and inner member 42 can be at least partly telescopically fitted within intermediate member 36.

Figure 2:
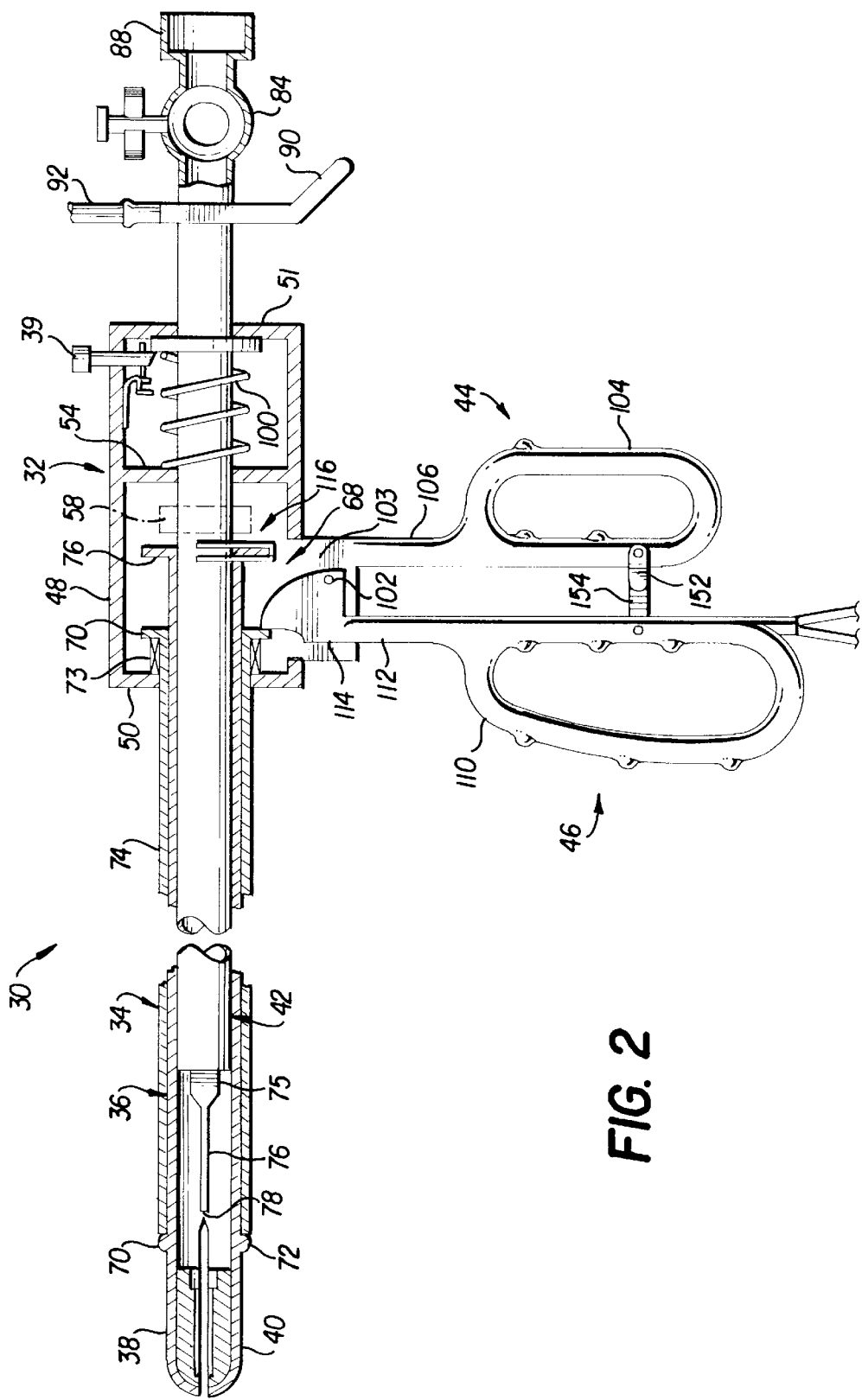
FIG. 2 is a cross-sectional view of the preferred embodiment taken along line 2—2.

As shown in FIG. 2, housing 32 is generally tubular with cylindrical sidewall 48 and front and rear walls 50 and 51 closing opposite ends of the cylindrical sidewall 58. Slotted opening 68 is formed in cylindrical sidewall 48 and extends longitudinally between the front wall 50 and intermediate wall 54, which divides housing 32 into two chambers, to permit movable handle 46 to pass therethrough. Fixed handle 44 extends from plate 103 extending from a portion of housing 32 proximate slot 68. Plate 103 can be formed integrally with housing 32 or can be fixedly attached to housing 32 to be stationary relative thereto.

Outer member 34 is open at both ends and extends through an opening in front wall 50 to terminate proximally at transverse flange 70 disposed between front wall 50 and intermediate wall 54 of housing 32. A distal end of outer member 34 can be blunt as shown, tapered, beveled or chamfered as desired or have any other suitable distal configuration. Preferably, outer member 34 is made of a substantially cylindrical length of a substantially rigid material, such as stainless steel or other medically acceptable plastic or metal material.

Intermediate member 36 includes tubular body 74 telescopically fitted within outer member 34. Tubular body 74 terminates proximally at transverse flange 76 disposed within housing 32 between flange 70 and intermediate wall 54; and, as best seen in FIGS. 3–7 which show intermediate member 36 removed from outer member 34 for illustrative purposes, a distal end of tubular body 74 is split longitudinally to form integral one-piece jaws 38 and 40 that oppose one another. Jaws 38 and 40 are normally biased apart as shown and respectively define opposed semicylindrical recesses 58 and 60 (see FIGS. 5 and 7) for carrying jaw inserts 62 and 64 respectively. Jaw inserts 62 and 64 can be permanently or removably secured within the semicylindrical recesses using adhesives, detents, or any other suitable method of attachment or can be formed with jaws 38 and 40 as an integral one-piece construction. Each of inserts 62 and 64 defines a grasping surface or tread 66 having a substantially flat portion suitable for grasping and manipulating anatomical tissue or holding instruments such as a needle. Also, a slot, groove 68, or other type of cavity can be formed in inserts 62 and 64 to permit passage of a distal end of an inner member as disclosed in the parent application. A repeated pattern of diamond-shaped protrusions is shown for tread 66. However, other surfaces such as those having parallel ribs or textured portions could be used. Wedge-like cams 70 and 72 are formed on respective exterior surfaces of jaws 38 and 40 and are distally spaced from the distal end of outer member 34 when jaws 38 and 40 are open. Cams 70 and 72 taper toward the joint region or junction where each jaw connects with the tubular body 74.

As best seen in FIG. 3, tubular body 74 of intermediate member 36 is preferably formed with jaws 38 and 40 as a single unitary part using a resilient medically-acceptable material such as a spring steel or plastic having suitable elastic properties for normally biasing the upper and lower of jaws 38 and 40 apart while permitting jaws 38 and 40 to be moved towards one another in response to axial forces acting on the jaws and/or cams as a result of relative movement between outer member 34 and intermediate member 36. Referring again to FIG. 2, it can be seen that bias member 73 is connected between flange 70 of outer member 34 and front wall 50 such that outer member 34 is normally biased in a proximal direction relative to intermediate member 36. Bias member 73 is shown as a helical coil spring disposed around intermediate member 36 and held in compression between the flange 70 and front wall 50. However, bias member 73 can be constituted of various other types of springs as well as other types of bias devices including tension springs, torsion springs, pan springs, leaf springs, rubber, plastic or magnets, for example.

Figure 10:
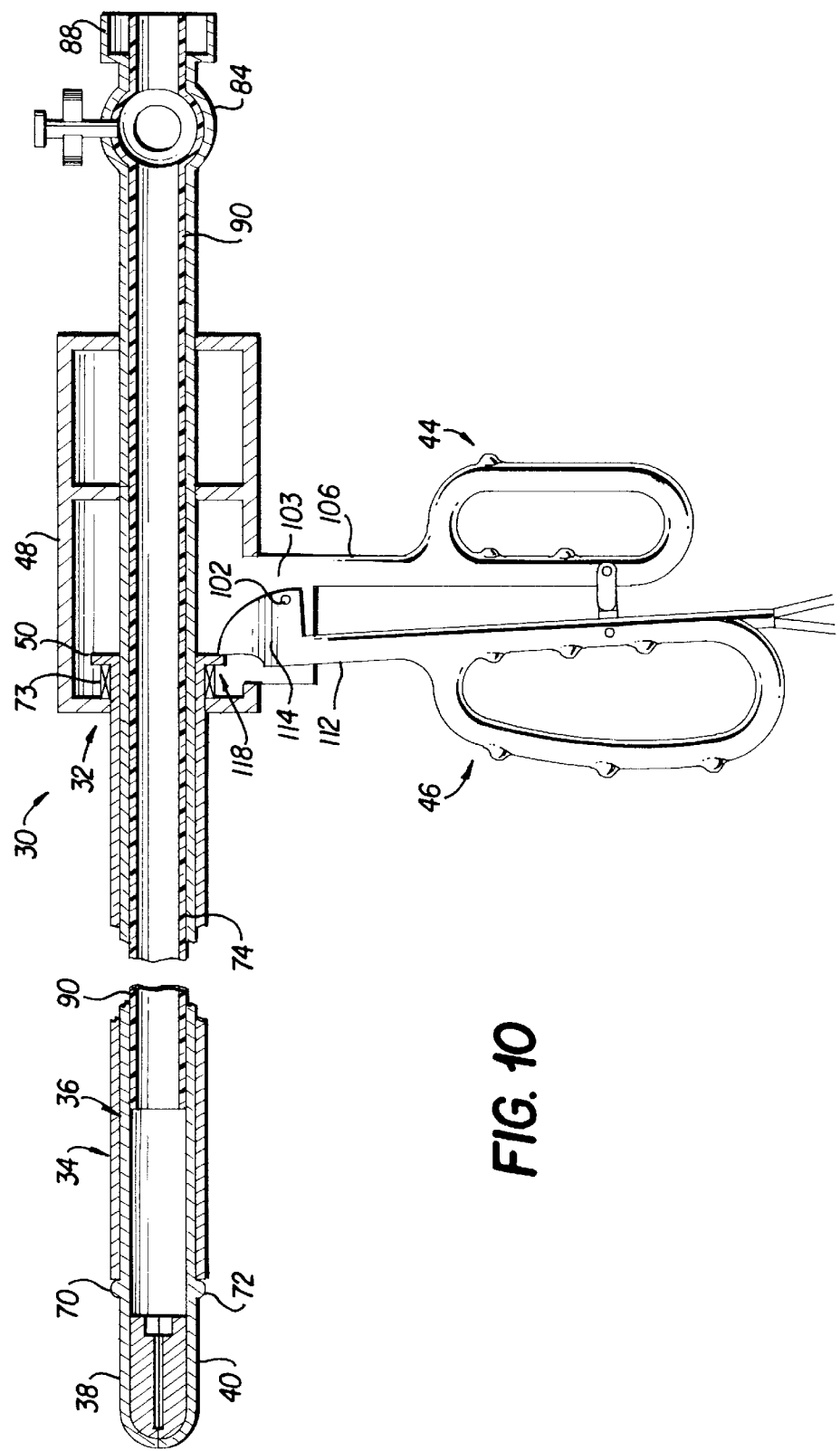
FIG. 10 illustrates the preferred embodiment without an inner member in cross-section with the jaws closed.

Inner member 42 such as that illustrated in FIG. 2, can be slidably disposed in intermediate member 34 to permit other surgical operations to be conducted with inner member 42 when advanced distally. While inner member 42 is illustrated as having a needle on a proximal end, various types of inner members 42, having various operating members such as a biopsy box, hook, scissors, electrodes, clip applicators, or the like, can be used. Inner member 42 has proximal aperture 88 and valve 84 to permit a channel through inner member 42 to be used for irrigation or suction by being coupled to the appropriate proximal suture. If inner member 42 is used, inner member 42 is biased toward a rear portion of housing 32 by biasing member 100 and passes through a hole formed in rear wall 51 of housing 32. Inner member 42 can have handle 90 for advancing inner member 42 and electrical connector 92 for permitting an electrical power source to be coupled to inner member 42 or other elements. In the modification illustrated in FIG. 10, there is no inner member shown and intermediate member 36 extends through a rear portion of housing 32 and has proximal aperture 88 and valve 84 formed thereon. Also electrically insulating member 90 is disposed inside intermediate member 36 to electrically insulate an inner member or other instrument advanced through a channel defined through intermediate member 36.

Movable handle 46 is pivotally mounted on pin 102 secured to mounting plate 103 extending outward from side wall 48 along an edge of slotted opening 68. Fixed handle 44 includes finger loop 104 configured to accommodate one or more fingers or the thumb of the surgeon and shank 106 connecting finger loop 104 with mounting plate 102. Movable handle 46 includes finger loop 110 configured to accommodate one or more fingers of the surgeon and shank 112 connecting finger loop 110 with flattened end portion 114 which extends into housing 12 towards flange 70 of outer member 34 through slotted opening 61. Intermediate member 36 is fixed to housing 32 by bracket 116. Note that the surgeon can grasp handles 44 and 46 either by placing finger in the finger loops or entirely around the finger loops.

A pair of mating protrusions 152 and 154 are carried at opposed locations on finger loops 104 and 110 respectively to lock handles 44 and 46 together when pressed towards one another a predetermined angular distance corresponding to a desired resultant position of jaws 38 and 40. Mating protrusions 152 and 154 are shown having serrated inside surfaces, but can have any other configuration to ratchet, mate frictionally and/or latch together when engaged.

Figure 11:
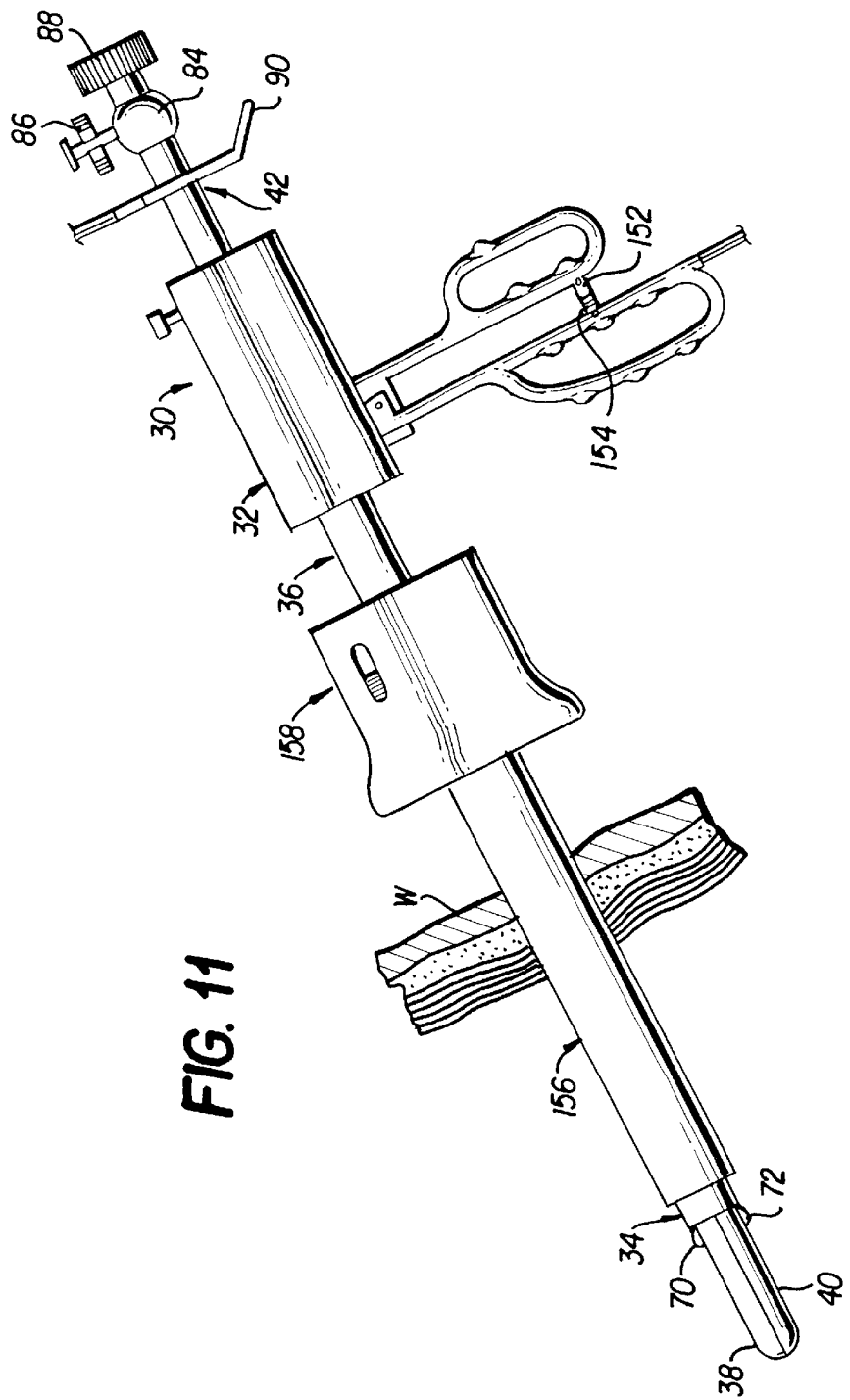
FIG. 11 illustrates the preferred embodiment in use.

Use of endoscopic instrument 30 of the present invention is illustrated in FIGS. 11–16. In FIG. 11 instrument 30 is shown being guided through portal sleeve 156 positioned in a wall W of an anatomical cavity. Instrument 30 is preferably passed through portal sleeve 156 with jaws 38 and 40 at least partly closed so that instrument 30 can be inserted without catching on anatomical tissue or snagging structure within portal sleeve 156. Since outer member 34 can be held by protrusions 152 and 154 in a position partly closing jaws 38 and 40, the surgeon need not exert any force on handles 44 and 46 during insertion.

With jaws 38 and 40 at least partly closed, endoscopic instrument 30 is inserted through portal sleeve 156 positioned within the anatomical cavity wall W, as shown in FIG. 11, to access an operative site within the anatomical cavity. Portal sleeve 156 can be positioned in the wall using any suitable penetrating technique, including those creating puncture sites by means of removable obturators such as trocars, and is shown carrying valve housing 158 at a proximal end to prevent the loss of pneumoperitoneum during insertion and withdrawal of endoscopic instrument 30. Visualization of the endoscopic procedure can be accomplished using a conventional endoscope (not shown) incorporated into endoscopic instrument 30, for example within the central channel defined through intermediate member 36, or inner member 42 if inner member 42 is used, or separately positioned within the anatomical cavity through a second portal sleeve located at another puncture site.

Figure 12:
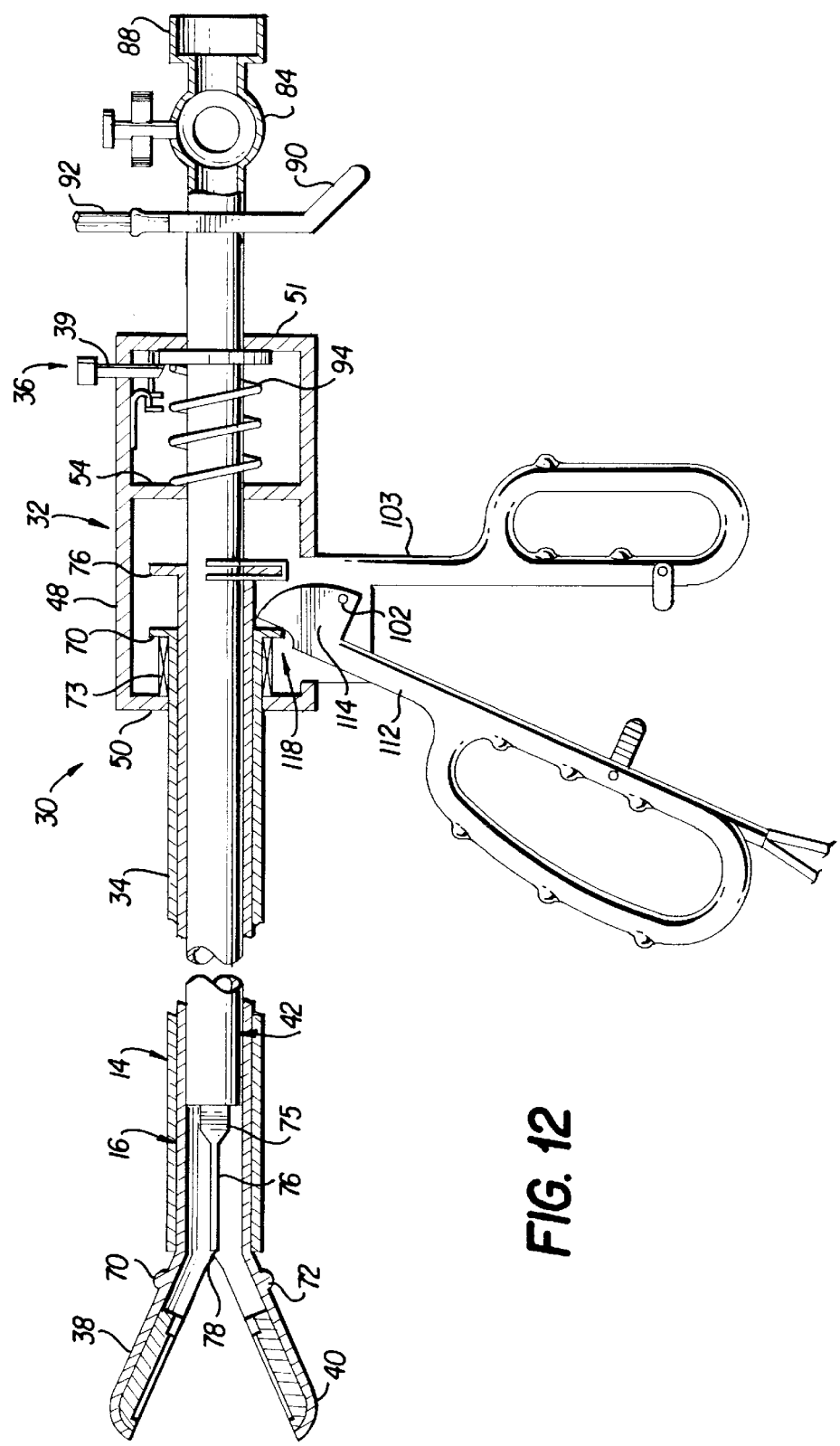
FIG. 12 illustrates the preferred embodiment in cross-section with the jaws open.

Endoscopic instrument 30 is advanced distally through portal sleeve 156 until jaws 38 and 40 emerge into the anatomical cavity. At this point, jaws 38 and 40 can be opened to permit visualization by an endoscope through the central channel or can remain closed in the case of using a separately positioned endoscope. If jaws 38 and 40 are to be opened, this is accomplished by exerting finger pressure on finger loops 104 and 110 to release protrusion 152 and 154 to spread finger loops 104 and 110 apart as shown in FIG. 12 due to the force of biasing member 73. Pivotal movement of finger loop 110 about pin 102 permits flange 70 to move proximally with respect to intermediate member 36. This causes the distal end of outer member 34 to slide off cams 70 and 72 in a proximal direction allowing jaws 38 and 40 to spread apart elastically, as illustrated in FIG. 12.

Figure 13:
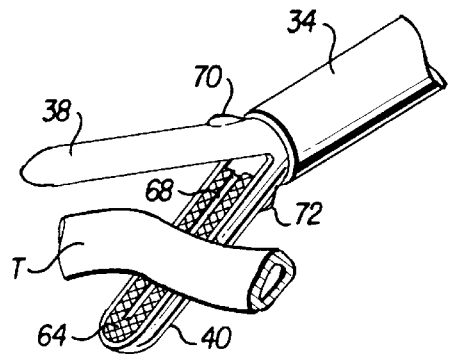
FIG. 13 illustrates the jaws prior to grasping tissue.

Instrument 30 can be moved within the anatomical cavity with jaws 38 and 40 in either the open or closed condition depending on the type of visualization utilized and the desirability of presenting a narrow or wide jaw profile during movement. In FIG. 13, jaws 38 and 40 are shown in the opened condition for being positioned around anatomical tissue T to be grasped. Tissue T is located between inserts 62 and 64 so that when jaws 38 and 40 are partly closed, for example by placing finger pressure on the handles 44 and 46, tissue T will be held securely within the small gap between the jaws 38 and 40 as shown in FIG. 14.

Figure 14:
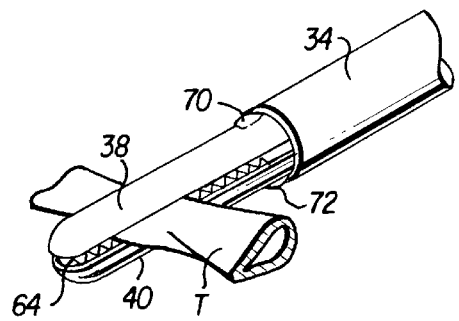
FIG. 14 illustrates the jaws grasping tissue.
Figure 16:
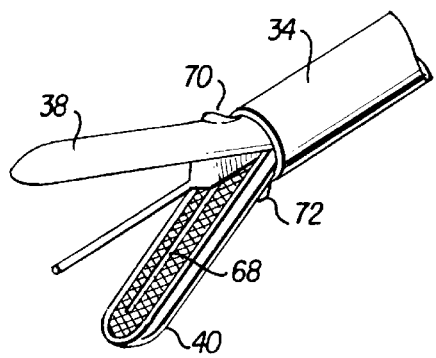
FIG. 16 illustrates the jaws in a open position with the inner member advanced.
Figure 15:
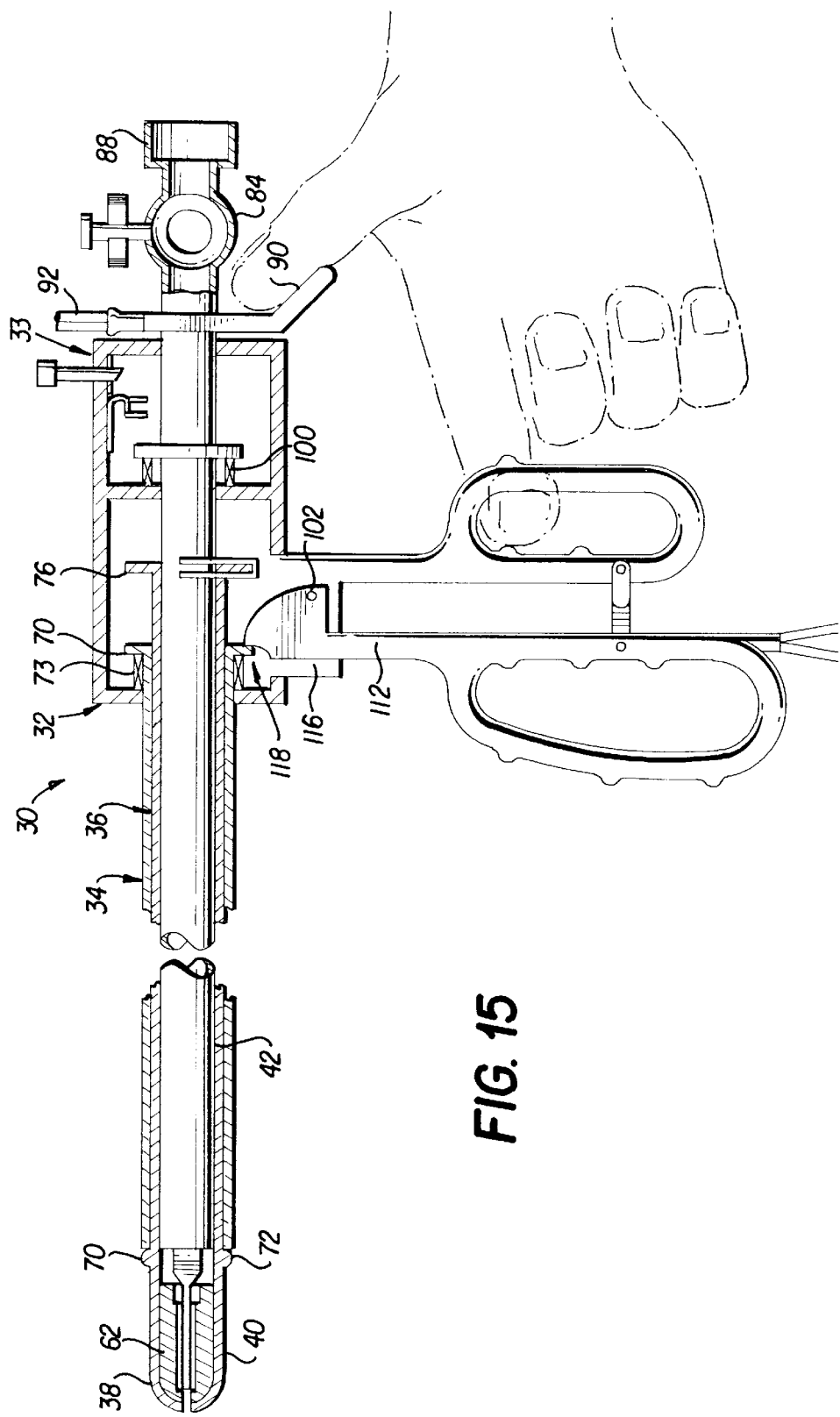
FIG. 15 illustrates the preferred embodiment in cross-section with an inner member advanced distally.

With tissue T firmly grasped between jaws 38 and 40 as illustrated in FIG. 14, inner member 42 can be advanced distally as shown in FIG. 15 to move an operating member disposed on the distal end of inner member 42, such as a blade, a needle, a cautery device, or the like (a needle is illustrated) into grooves 68, or the like formed in inserts 62 and 64 thereby performing an operation on the anatomical tissue T held between jaws 38 and 40. Also, inner member 42 can be advanced with the jaws open as illustrated in FIG. 16.

Inner member 42 is hollow and can thus be utilized for creating suction during the procedure, performing aspiration or irrigation or to facilitate passage of additional instruments or fluids into the anatomical cavity as desired. As noted above, when inner member 42 is not used, the channel formed in intermediate member 36 can be used for the passage of instruments or for creating suction, performing aspiration or irrigation or other back up procedures.

Tissue can be grasped and securely held with jaws 38 and 40 in a partly closed state. However, for certain procedures it may be desirable to draw jaws 38 and 40 completely together, with or without objects held between the jaws. Jaws 38 and 40 can be closed completely or clamped together by drawing finger loops 104 and 110 towards one another until the distal end of outer member 34 slides further distally over cams 70 and 72 to force jaws 38 and 40 into close contact with one another. If tissue or some other object is disposed between jaws 38 and 40, advancement of outer member 34 over cams 70 and 72 will result in greater compression of the object. When finger loops 104 and 110 are drawn sufficiently close to one another, mating protrusions 152 and 154 will be engaged, locking handles 24 and 26 in their current position. If mating protrusions 152 and 154 are ratcheted as shown, various degrees of compression can be achieved and maintained without continuous finger pressure being applied.

Figure 8:
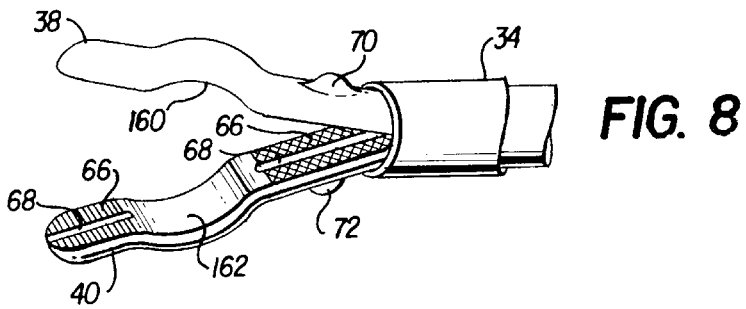
FIG. 8 illustrates a modified jaw.
Figure 9:
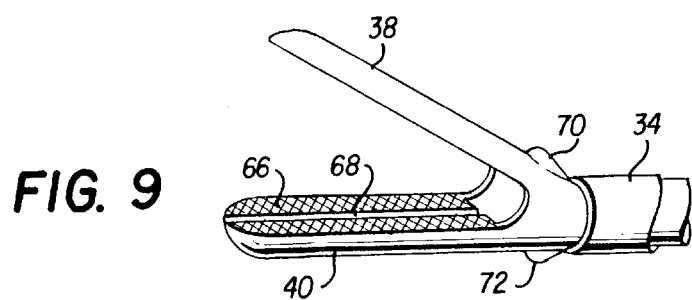
FIG. 9 illustrates another modified jaw.

As shown in FIG. 8, jaws 38 and 40 can have recessed portions 160 and 162 respectively to accommodate a tubular tissue or the like without compressing the tubular tissue when jaws 38 and 40 are closed. As shown in FIG. 9, jaw 40 can be fixed and jaw 38 can be movable.

Figure 17:
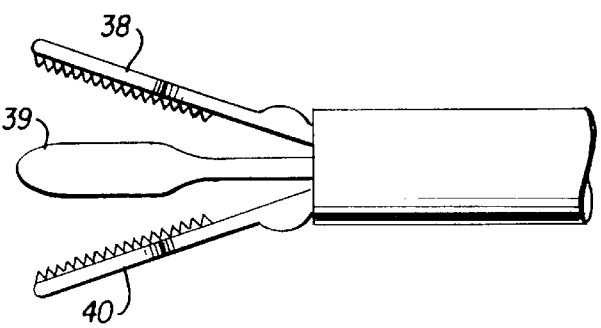
FIG. 17 is a plan view of modified jaws.
Figure 18:
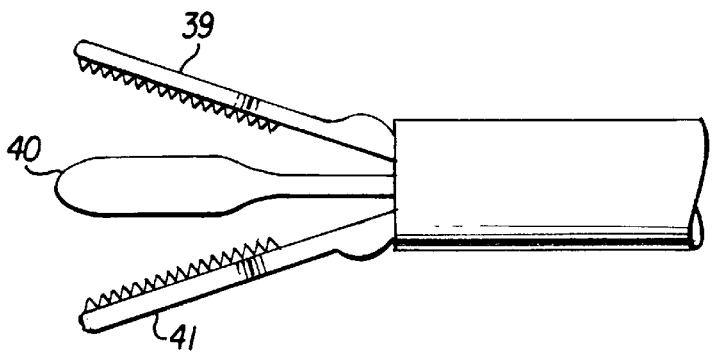
FIG. 18 is a side view of the jaws of FIG. 17.

The modification illustrated in FIGS. 17 and 18 includes opposing jaws 38 and 40, as in the configurations disclosed above, and auxiliary jaws 39 and 41 which oppose one another and move along a plane that is essentially perpendicular to the plane along which jaws 38 and 40 move. When closed, jaws 38, 39, and auxiliary jaws 40, and 41 meet along a central axis. All of jaws 38, 39, and auxiliary jaws 40, and 41 have substantially flat grasping surfaces.

Figure 19:
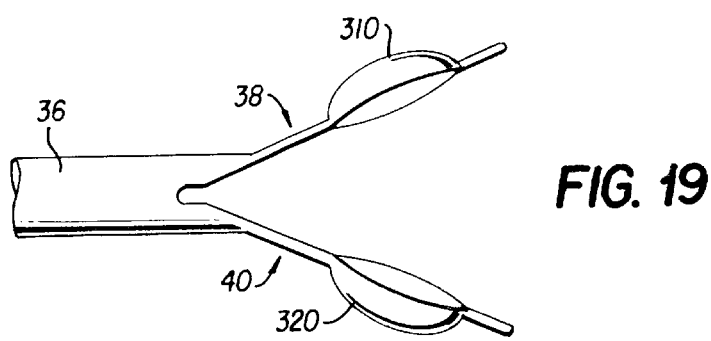
FIG. 19 illustrates modified jaws.

In the modification illustrated in FIG. 19, jaws 38 and 40 have biopsy boxes 310 and 320, in the form of cupped portions, formed in substantially flat grasping surfaces respectively. Biopsy boxes 310 and 320 have cutting edges formed thereon to cut a tissue biopsy sample when jaws 38 and 40 are closed with tissue therebetween. Biopsy boxes 310 and 320 can be of any desired shape to cut a sample of a desired shape. Distal portions of jaws 38 and 40 extend beyond biopsy boxes 310 and 320 to permit tissue manipulation with the distal portions without cutting a biopsy sample.

Figure 20:
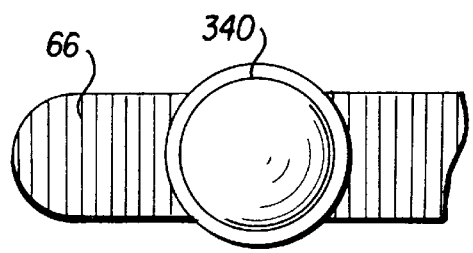
FIG. 20 is a plan view of one of the jaws of FIG. 21.
Figure 21:
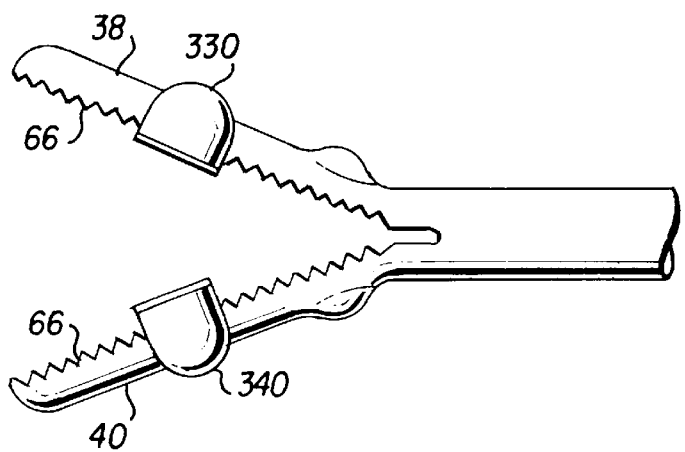
FIG. 21 is a side view of modified jaws.

In the modification illustrated in FIGS. 20 and 21, jaws 38 and 40 have substantially flat grasping surface or tread 66 and biopsy boxes 330 and 340 formed therein. Biopsy boxes 330 and 340 of this modification occupy only a small portion of the gripping surface, as illustrated in FIG. 20, so that treads 66 can be used more efficiently for tissue manipulation, grasping a needle, or the like. Of course, the jaws can be of any shape to provide tread 66 suitable for grasping a desired object and can have indentations or the like for grasping and orienting thin objects such as needles. Also, removable jaw inserts can have the tread and biopsy boxes formed therein.

Figure 22:
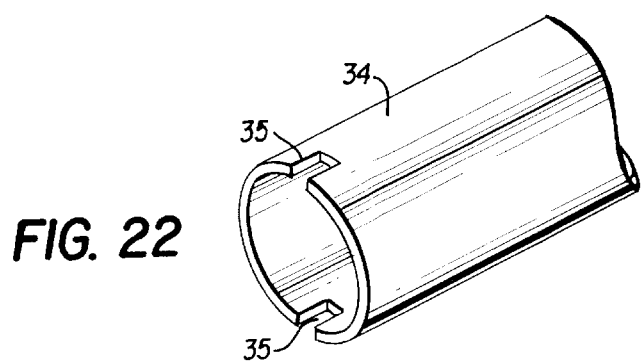
FIG. 22 illustrates a distal end of a modified outer member.

Jaws 38 and 40 of the preferred embodiment are formed integrally on intermediate member 36. However, the jaws can be formed on a separate tubular portion that is attached to a distal end of intermediate member 36 by a coupling defined by detents, welding, pressure fitting, screw threads, or the like. Also, as shown in FIG. 22, which illustrates a modified distal end of outer member 34, slots 35 can be formed in outer member 34 to receive cams 70 and 72. This helps to maintain alignment of jaws 18 and 20.

From the above, it will be appreciated that the endoscopic instrument of the present invention permits multiple functions to be performed endoscopically by use of a member with jaws having substantially flat grasping surfaces for grasping or manipulating objects such as anatomical tissue or needles and an operating channel defined in the instrument that can accommodate an inner member telescopically or be used for suction, irrigation, or other backup operations. The inner member can have various end effectors or operating members such as single-edge cutting blades, scissors, biopsy containers, cauteries, solid and hollow needles, ligatures, hooks and/or endoscopes, for example, for performing at least one of the functions of cutting, collecting tissue for a biopsy, penetrating, injecting fluids, creating suction, aspirating, irrigating, grasping, manipulating, hooking, dissecting and cauterizing, for example.

The intermediate member and jaws of the forceps unit can be formed as an integral one-piece construction, or the jaws can be formed separately, and can be movably disposed within an outer tubular member to permit sliding movement of the outer tubular member over the jaws. The outer member and intermediate member can be on a housing and coupled using any suitable handle mechanism and linkages for producing relative movement between the jaws and the outer tubular member. Because the instrument has a channel, the forceps unit can be positioned within an anatomical cavity with various inner members being advanced distally through the instrument for forming different functions. The inner members can also have hollow tubular shafts open at a distal end for facilitating visualization with a conventional endoscope, illumination with fiber optics or other suitable light sources, for passage of implements such as blades or ligature appliers to cooperate with instruments mounted at the distal end of the inner member tubular shaft, and/or for introducing or collecting fluids prior to, during or after an operative step, such as cutting or puncturing, is completed. The outer member can be substantially larger than the inner member in cross-sectional area to permit the operating channel to extend through the outer member at a position not coaxial with the inner member.

The jaws of the present invention can be straight, curved and/or angled and can have integrally formed or removable inserts with configurations for grasping and holding tissue and objects such as needles. Note that, while the jaws are discussed generally above as part of forceps, the jaws can be used to grasp a needle or other object for suturing or the like. The jaws or inserts can have any combination or number of longitudinal grooves formed in the inserts for accommodating operating members such as blades, scissors, biopsy tools, needles, hooks, surgical clips or any other types of medical implements. The grooves can extend part way to define stops or abutments limiting distal movement of the end effectors or can extend the complete length of the inserts to form openings or apertures at a distal end of the jaws to allow passage of the end effectors beyond the distal end of the jaws when the jaws are closed. The jaws can have any shape in cross-section when closed, including circular, elliptical, rectangular and polygonal configurations, and can have opposed arcuate or concave portions for clamping tubular objects without compressing the objects.

Integral blades can be carried by one or both jaws and centrally located for cutting anatomical tissue or can be offset laterally from the central longitudinal axis of the jaws to permit better visualization and the formation of a longitudinal groove for passage of other operating members through the jaws. If a single blade is carried by one jaw, the other jaw can carry an opposed blade in a manner to permit sliding contact with scissor-like cutting, direct abutment of cutting edges to produce a chopping cut, and/or can form a pocket for receiving the cutting edge of the opposed blade to permit partial or complete closure of the jaws together. Furthermore, any blade of a scissor device carried by the jaws or an inner member of the present invention can be provided with a sharp hook extending transversely from the distal end of the blade in opposed relation to the other blade.

When the jaw inserts are removable, the empty cavities defined by the jaws can be used for accommodating cartridges holding surgical staples or clips such that by closing the jaws the staples or clips can be applied to anatomical tissue. Moreover, the elongate tubular structure of the inner member permits a series of cartridges to be carried therein for being applied individually within the anatomical cavity without removal of the inner member.

An electrical connector can be provided to permit bipolar or unipolar cauterization using the jaws or other portions of the instrument that are electrically isolated in a known manner. The electrical connector can be disposed on the housing or at any other appropriate location. For example, an electrical connection could be made directly with the housing of the forceps to utilize the forceps jaws as conductive elements for performing electrosurgery or the electrical connector can be on one of the handles. Also, inner surfaces of any of the tubular members, can be electrically insulated to permit passage of electrosurgical instruments therethrough.

The handles and linkages shown and described herein for sliding the outer member over the jaws are exemplary of the types of conventional handle mechanisms suitable for performing the function of closing the jaws. However, the handles can have any configuration for producing relative movement between the outer and intermediate members, including two pivoted legs with finger loops and sliding brackets as disclosed in the parent application, one fixed and one pivoted leg with finger loops, a pistol grip with a movable trigger, or resilient U-shaped members connected between outer and intermediate members. Moreover, the handles can have any orientation relative to the longitudinal axis of the instrument including, for example, substantially transverse orientations whereby the handles extend transversely from a sidewall of the housing or substantially longitudinal orientations whereby the handles extend longitudinally from a rear wall of the housing and are operated like a scissors or even rotatable configurations whereby the handles can be moved between transverse and longitudinal orientations as desired by selectively disengaging the handles from the jaws. Suitable linkages include brackets with sliding motion, gears and/or racks mounted on or between handles and the outer and intermediate members, pulleys and cords or any other direct or indirect coupling mechanisms.

The intermediate and outer members can be frictionally fitted to maintain a position by resisting relative movement, can be biased apart with a bias member such as a torsion spring connected between the handles or a helical coil spring disposed around the intermediate member and held in compression between intermediate and outer member flanges, or can be biased together as desired. If the outer member is biased relative to the intermediate member, a mechanism can be provided for locking/releasing the bias member to permit the outer tubular member to be maintained at any position relative to the jaws, for example by frictional engagement.

The components of the endoscopic instrument of the present invention can be made of any suitable, medical grade materials to permit sterilization for re-use or for single patient use. The components can be made of multiple parts of various configurations and materials to reduce cost.

The features of the various embodiments described above can be combined in any manner desired dependent upon the operational requirements of the procedure to be performed and the complexity of the endoscopic instrument. The operating channel can be used for any desired purpose depending on the procedure being performed. The various tubular members can have any appropriate cross-sectional shape.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A surgical instrument comprising
   a tubular outer member having a proximal end and terminating distally at a distal end and having an operating channel defined therethrough;
   an intermediate member having a body disposed at least partly within said outer member, said body having a proximal end and a distal end, a pair of opposed jaws each having a substantially flat grasping surface and being disposed on said distal end of said body and being resiliently biased apart;
   a handle coupled with at least one of said jaws and configured to move said pair of opposed jaws between open and closed positions.

2. An instrument as recited in claim 1 wherein said body is tubular and said operating channel extends through said body.

3. An instrument as recited in claim 1, wherein said jaws are formed integrally with said body.

4. An instrument as recited in claim 1, wherein said jaws are formed separately from said body and are attached to said body by coupling means.

5. An instrument as recited in claim 1, wherein each of said jaws define a recessed portion and an insert is removably disposed in each recessed portion.

6. An instrument as recited in claim 2, further comprising an inner member movably disposed in said tubular body, said inner member having an end effector on a distal end for performing a medical procedure.

7. An instrument as recited in claim 1, wherein both of said jaws are movable.

8. An instrument as recited in claim 1, wherein one of said jaws is fixed and one of said jaws is movable.

9. An instrument as recited in claim 1, wherein at least one of said jaws has an arcuate portion formed therein for receiving tissue without compressing the tissue.

10. An instrument as recited in claim 1, further comprising a pair of opposed auxiliary jaws, said auxiliary jaws move in a plane that is transverse to a plane in which said jaws move.

11. An instrument as recited in claim 1, wherein said jaws have biopsy boxes formed therein.

12. An instrument as recited in claim 4, wherein a biopsy box is formed in said inserts.

13. A multifunctional instrument for use in performing procedures within an anatomical cavity comprising
    a handle;
    an elongate tubular member having a proximal end coupled with said handle for being disposed externally of the anatomical cavity and a distal end for being disposed within the anatomical cavity and carrying a pair of opposed, relatively movable jaws, said elongate tubular member defining a channel permitting access to an operative site within the anatomical cavity from outside the body;

said jaws being movable relative to one another by manipulation of said handle to perform grasping operations, each jaw having a substantially flat grasping surface.

14. A multifunctional instrument for use in performing procedures within an natomical cavity as recited in claim 13 wherein said jaws are biased apart toward an open position and further comprising an outer tubular member disposed telescopically around said elongate tubular member and having a proximal end coupled with said handle and a distal end movable relative to said elongate tubular member by manipulation of said handle between a retracted position allowing said jaws to open and an extended position causing said jaws to close.

15. A multifunctional instrument for use in performing procedures within an anatomical cavity as recited in claim 13 and further comprising a coupling detachably coupled with said elongate tubular member for mounting said opposed, relatively movable jaws.

16. A multifunctional instrument for use in performing procedures within an anatomical cavity as recited in claim 13 wherein at least one of said jaws is electrically conductive and further comprising an insulated connector coupled with said electrically conductive jaw for connecting a cauterizing current to said blade.

17. A method of conducting a surgical procedure comprising the steps of:

introducing a member having a body and moveable jaws disposed on a distal end of said body into an area proximate tissue, each of said jaws having a substantially flat grasping surface;

manipulating the tissue with said jaws;

communicating with the area proximate the tissue through a channel defined through an outer member disposed around the member.

18. A method as recited in claim 17 wherein, in said communicating step, said channel passes through said body of said member.

19. A method as recited in claim 17 further comprising introducing an inner member having an end effector through said channel.

20. A surgical instrument comprising:

a tubular outer member having a proximal end and terminating distally at a distal end and having an operating channel defined therethrough;

an intermediate tubular member having a body disposed at least partially within the outer member, the body having a proximal end and a distal end and a pair of opposed jaws, each having a substantially flat grasping surface and being disposed on the distal end of the body and being resiliently biased apart; and a handle coupled with at least one of the jaws and configured to move the pair of opposed jaws between open and closed positions.

* * * * *